(12) United States Patent
Kiani et al.

(10) Patent No.: US 6,526,300 B1
(45) Date of Patent: Feb. 25, 2003

(54) PULSE OXIMETER PROBE-OFF DETECTION SYSTEM

(75) Inventors: Massi E. Kiani, Niguel, CA (US); Mohamed K. Diab, Mission Viejo, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 09/595,081

(22) Filed: Jun. 16, 2000

Related U.S. Application Data

(60) Provisional application No. 60/140,000, filed on Jun. 18, 1999.

(51) Int. Cl.$^7$ .................................................. A61B 5/00
(52) U.S. Cl. ...................................... 600/322; 600/344
(58) Field of Search .................................. 600/309–310, 600/322–324, 316, 344; 356/39–42

(56) References Cited

U.S. PATENT DOCUMENTS

| | | | | |
|---|---|---|---|---|
| 4,295,475 A | * | 10/1981 | Torzala | 600/549 |
| 4,331,161 A | * | 5/1982 | Patel | 600/549 |
| 4,561,440 A | * | 12/1985 | Kubo et al. | 607/89 |
| 5,370,114 A | * | 12/1994 | Wong et al. | 600/322 |
| 5,469,845 A | * | 11/1995 | DeLonzor et al. | 600/372 |
| 5,503,148 A | * | 4/1996 | Pologe et al. | 600/323 |
| 6,035,223 A | * | 3/2000 | Baker, Jr. | 600/323 |

\* cited by examiner

*Primary Examiner*—Eric F. Winakur
*Assistant Examiner*—Matthew Kremer
(74) *Attorney, Agent, or Firm*—Knobbe, Martens, Olson & Bear, LLP

(57) ABSTRACT

The present invention provides a number of improvements that can be incorporated into a pulse oximeter probe to detect when a probe has become dislodged from a patient and/or to prevent a probe-off condition. A probe-off condition occurs when the optical probe becomes partially or completely dislodged from the patient, but continues to detect an AC signal within the operating region of the pulse oximeter. In one aspect, the present invention provides electrical contacts that contact the skin of a patient when the probe is properly attached. In another aspect, the present invention provides a number of louvers placed in front of the sensor's photodetector to filter out oblique light rays that do not originate from a point in front of the detector. Accordingly, if the emitter and photodetector are not properly aligned, the photodetector will not produce a signal within the valid operating range of the pulse oximeter. In accordance with a method of the present invention the pulse oximeter can sound an alarm or display a warning if it determines that the probe is not properly attached to the patient.

47 Claims, 15 Drawing Sheets

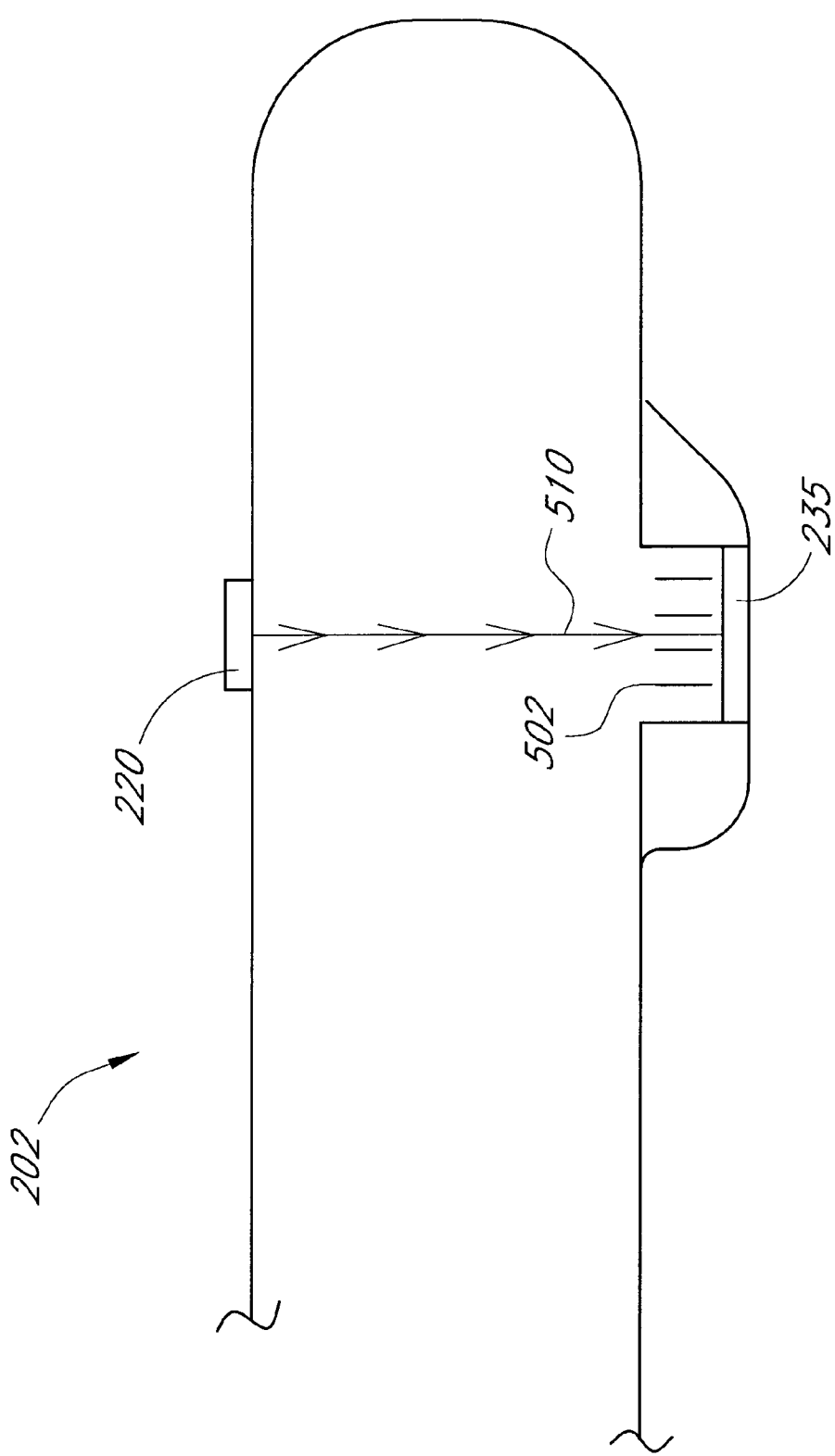

PULSE OXIMETER PROBE-OFF DETECTION SYSTEM

Applicant claims priority to prior filed Provisional Application No. 60/140,000 filed Jun. 18, 1999.

BACKGROUND OF THE INVENTION

1. Field of the Invention

The present invention relates to optical probes that can be attached to the finger, toe, or appendage of a patient. More particularly, the present invention relates to devices and methods for identifying when a probe has become dislodged from a patient.

2. Description of the Related Art

Oximetry is the measurement of the oxygen status of blood. Early detection of low blood oxygen is critical in the medical field, for example in critical care and surgical applications, because an insufficient oxygen supply can result in brain damage and death in a matter of minutes. Pulse oximetry is a widely accepted noninvasive procedure for measuring the oxygen saturation level of arterial blood, an indicator of oxygen supply. A pulse oximetry system generally consists of a probe attached to a patient, a monitor, and a cable connecting the probe and monitor. Conventionally, a pulse oximetry probe has both red and infrared (IR) light-emitting diode (LED) emitters and a photodiode detector. The probe is typically attached to a patient's finger or toe, or a very young patient's foot. For a finger, the probe is configured so that the emitters project light through the fingernail, the arteries, vessels, capillaries, tissue and bone. The photodiode is positioned opposite the LED so as to detect the LED transmitted light as it emerges from the finger tissues.

The pulse oximetry monitor (pulse oximeter) determines oxygen saturation by analyzing the differential absorption by arterial blood of the two wavelengths emitted by the probe. The pulse oximeter alternately activates the probe LED emitters and reads the resulting current generated by the photodiode detector. This current is proportional to the intensity of the detected light. The pulse oximeter calculates a ratio of detected red and infrared intensities, and an arterial oxygen saturation value is empirically determined based on the ratio obtained. The pulse oximeter contains circuitry for controlling the probe, processing the probe signals and displaying the patient's oxygen saturation and pulse rate. A pulse oximeter is described in U.S. Pat. No. 5,632,272 assigned to the assignee of the present invention.

SUMMARY OF THE INVENTION

The present invention provides a number of improvements that can be incorporated into a pulse oximeter probe to detect when a probe has become dislodged from a patient and/or to prevent a probe-off condition. A probe-off condition occurs when the optical probe becomes partially or completely dislodged from the patient, but may continue to detect an AC signal within the operating region of the pulse oximeter.

In one aspect, the present invention provides a number of electrical contacts that contact the skin of a patient when the probe is properly attached. The pulse oximeter can check the continuity through the contacts to determine whether the probe is properly attached. If the probe is not properly attached, the pulse oximeter can identify a probe-off condition even though the oximeter measures an AC signal that appears like the probe is still attached.

In another aspect, the present invention provides a number of louvers placed in front of the probe's photodetector to filter out oblique light rays that do not originate from a point in front of the detector. If the probe becomes dislodged, the emitter will not likely remain in front of the photodetector. If the emitter and photodetector are not properly aligned, the photodetector will not produce a signal within the valid operating range of the pulse oximeter. The louvers prevent light from an oblique angle from reaching the photodetector and creating a false signal that might be interpreted by the pulse oximeter as a physiological signal. Accordingly, the pulse oximeter can determine that a probe has become dislodged when the photodetector does not produce a valid signal. Furthermore, probe-off conditions can avoided since oblique light rays are not able to reach the photodetector to produce an apparently valid signal.

BRIEF DESCRIPTION OF THE DRAWINGS

Referring now to the drawings in which like reference numbers represent corresponding components throughout:

FIG. 5B illustrates a properly attached probe wherein a number of louvers are placed in front of the detector assembly;

DETAILED DESCRIPTION OF THE PREFERRED EMBODIMENT

To compute peripheral arterial oxygen saturation, denoted $Sp_aO_2$, pulse oximetry relies on the differential light absorption of oxygenated hemoglobin, $HbO_2$, and deoxygenated hemoglobin, Hb. This differential absorption is measured at the red and infrared wavelengths of the probe. In addition, pulse oximetry relies on the pulsatile nature of arterial blood to differentiate hemoglobin absorption from absorption of other constituents in the surrounding tissues. Light absorption between systole and diastole varies due to the blood volume change from the inflow and outflow of arterial blood at a peripheral tissue site. The tissue site might also comprise skin, muscle, bone, venous blood, fat, pigment, etc., each of which absorbs light. Blood oxygen saturation measurements are based upon a ratio of the time-varying or AC portion of the detected red and infrared signals with respect to the time-invariant or DC portion. This AC/DC ratio normalizes the signals and accounts for variations in light pathlengths through the measured tissue.

Figure 1:
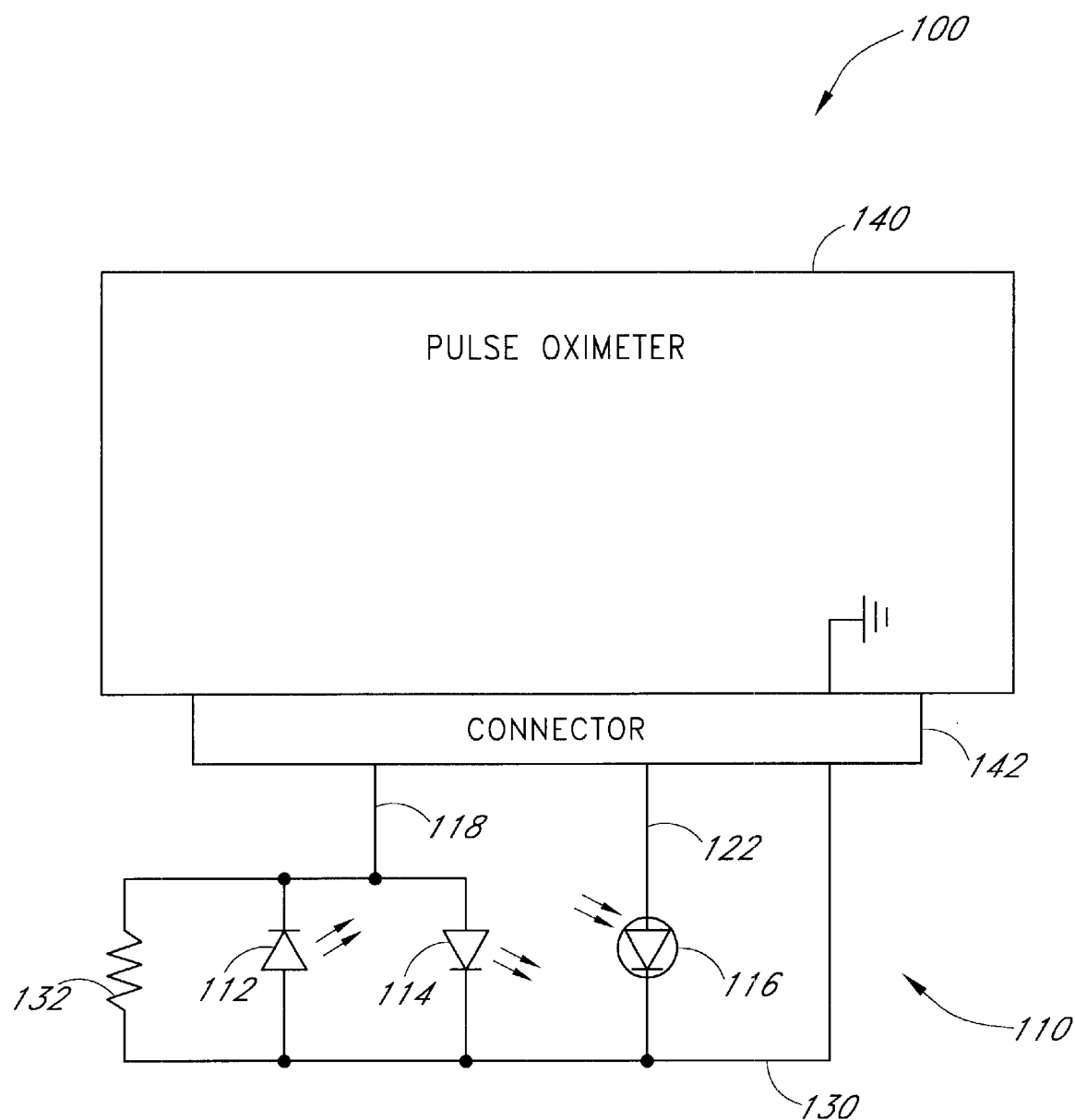
FIG. 1 illustrates a schematic of one embodiment of a pulse oximeter system.

As reproduced in FIG. 1, a schematic of one embodiment of a pulse oximeter system 100 is disclosed in U.S. Pat. No. 5,758,644 (the '644 patent), assigned to the assignee of the present application and incorporated herein by reference. The system 100 comprises a pulse oximeter 140, which is attached through a connector 142 to a probe 110. The probe 110 comprises a first LED 112, a second LED 114 and a photodetector 116. The first and second LEDs 112 and 114 are connected back-to-back and share a common electrical connection 118. The photodetector 116 has its own electrical connection 122. Each of the LEDs 112 and 114 and the photodetector 116 are connected at their outputs to a common ground electrical connection 130. The two LEDs 112 and 114 are preferably configured to produce different wavelengths of light, which pass through the flesh of a patient to be detected by the photodetector 116. The oximeter 140 can select the LED to be driven by applying either a positive or negative voltage to the connection 118. A coding resistor 132 has a resistance that can measured by the pulse oximeter 140 to determine the particular characteristics of the probe 110. The coding resistor 132 is coupled in parallel with the first LED 112 or the second LED 114. The resistor 132 can be used to indicate the operating wavelength of the first and second LEDs 112 and 114, or to indicate the type of probe. In order to read the coding resistor 132, the pulse oximeter 140 drives the first LED 112/coding resistor 132 combination at a level that is low enough that the LED draws insignificant current. At this level, significantly all of the current flows through the coding resistor 132 and the pulse oximeter 140 can determine the value of the resistor in accordance with Ohm's law. By configuring the coding resistor 132 in parallel with one of the LEDs 112, 114, the added expense of an additional lead connecting the pulse oximeter 140 to the probe 110 can be saved.

Figure 2A:
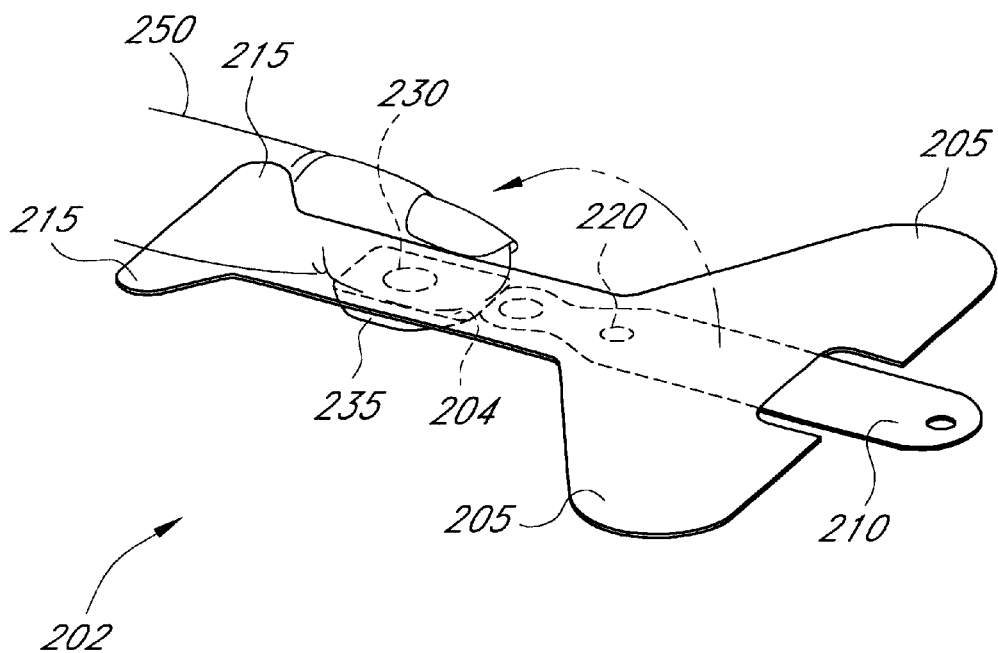
FIGS. 2A–B depict an optical probe and the attachment of the optical probe on the fingertip of an adult patient.
Figure 2B:
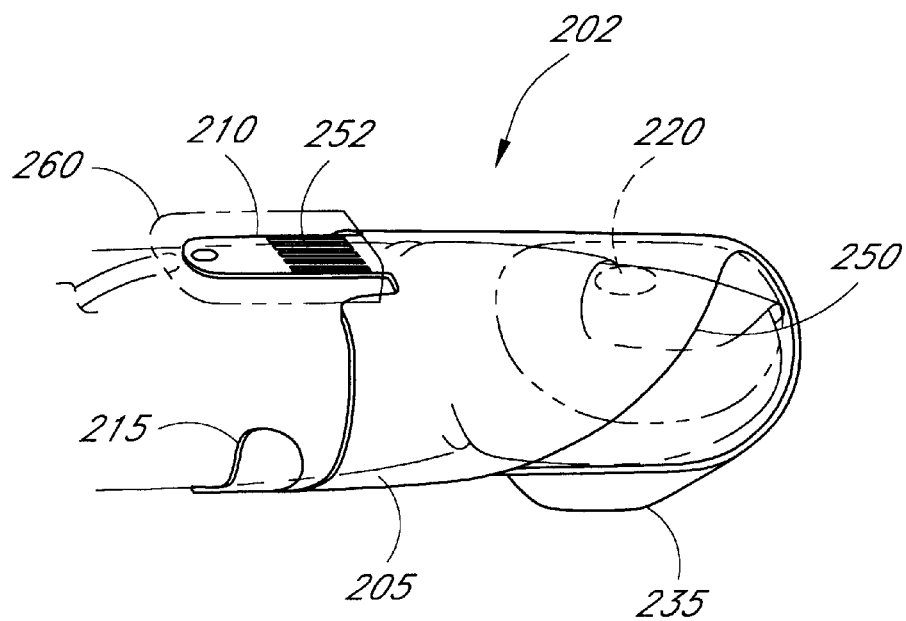

One embodiment of a disposable probe for use with pulse oximetry systems is disclosed in U.S. Pat. No. 5,782,757, assigned to the assignee of the present application and incorporated herein by reference. FIGS. 2A–B depict the optical probe 202 and the attachment of the optical probe 202 on the fingertip 250 of an adult patient. The disposable optical probe 202 is designed to fit comfortably onto a patient's fingertip. As illustrated in FIG. 2A, the probe 202 includes a central portion 204, a pair of adhesive flanges 205 extending from the central portion 204, a connector portion 210 situated between the flanges 205, and a pair of smaller adhesive flaps 215 extending from the central portion 204 on the end of the optical probe 202 opposite from a connector tab 210. The probe 202 further includes an emitter aperture 220 with a number of emitters (e.g., a light-emitting diodes) positioned within the central portion 204 close to the connector portion 210, and a detector aperture 230 which allows light to pass through the detector aperture 230 to a detector assembly 235. An adult fingertip 250 is shown in phantom in FIG. 2A to illustrate the position at which the fingertip 250 is placed when the probe 202 is to be fastened onto the fingertip 250 for use. Although not depicted specifically in FIGS. 2A–2B, the probe 202 is typically fabricated from multiple layers.

FIG. 2B illustrates the probe 202 fastened onto the fingertip 250. As shown in FIG. 2B, the probe 202 folds to conform to the very end of the fingertip. The adhesive flaps 205 fold downward (in the illustration of FIG. 2B) to wrap around the fingertip 250 while the adhesive flaps 215 fold upward (in the illustration of FIG. 2B) about a portion of the circumference of the fingertip 250 to provide support. As shown in FIG. 2B, when the probe 202 is folded about the fingertip 250, the emitters located within the probe are spaced opposite the detector assembly 235 such that light from the emitters passes through the emitter aperture 220, through the finger 250 and is incident upon the detector assembly 235 through the detector aperture 230.

FIG. 2B depicts a receiving connector portion 260 which engages with contacts 252 on the connector 210 to provide an electrical connection between the optical probe 202 and the pulse oximeter 140. Once the optical probe 202 is securely fastened to the fingertip 250 and the connector 210 provides an electrical connection between the optical probe 202 and digital signal processing circuitry, signals are detected from the detector 235 and transmitted to the processing circuitry via the connector 260.

A probe-off condition occurs when the optical probe becomes partially or completely dislodged from the patient, but continues to detect an AC signal within the operating region of the pulse oximeter. Probe-off errors are serious because the pulse oximeter may display a normal saturation when, in fact, the probe is not properly attached to the patient, potentially leading to missed desaturation events. Failure to detect a probe-off condition is the result of the probe detector receiving light directly from the emitters without transmission through the patient's tissue.

Figure 3A:
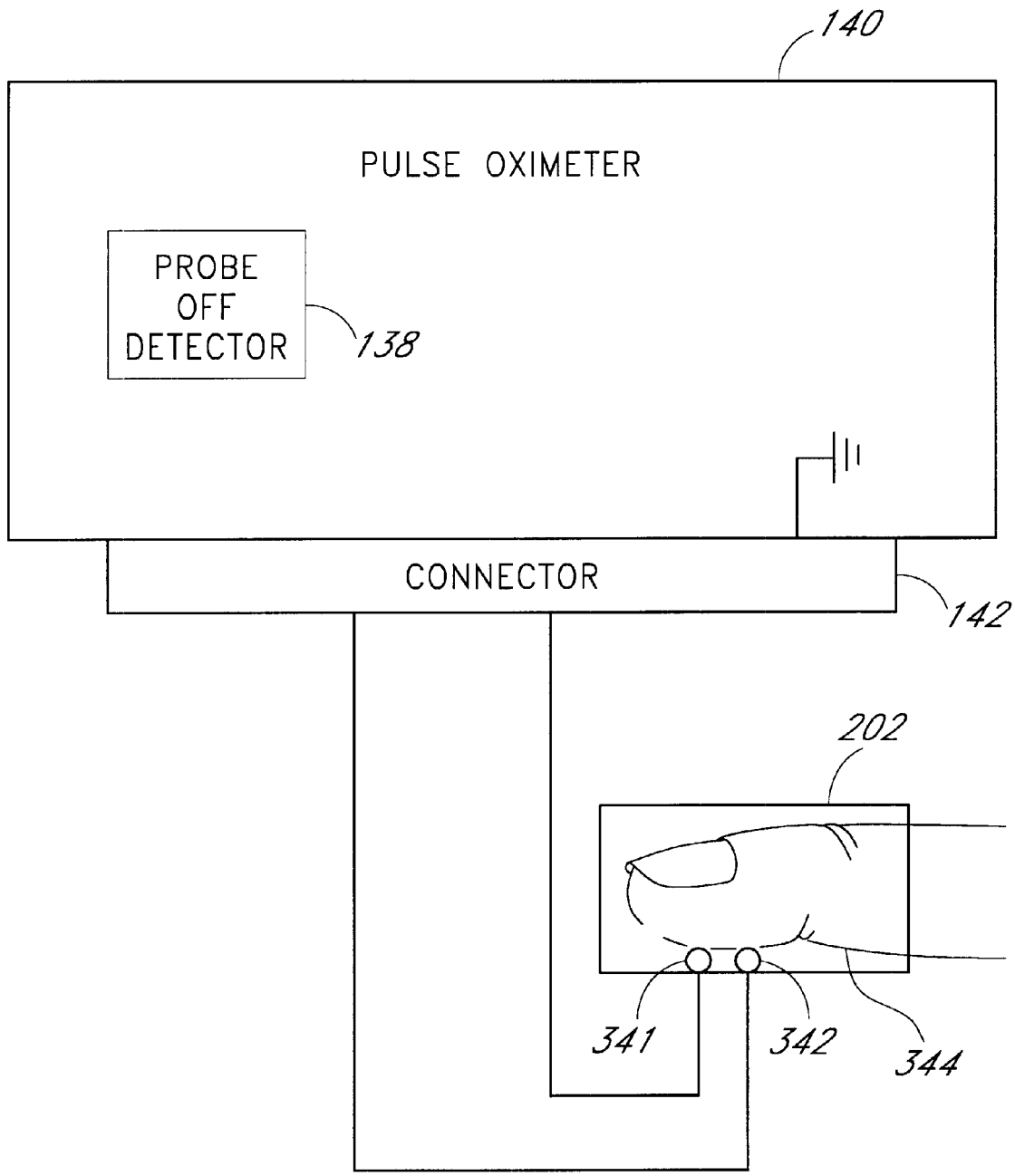
FIG. 3A illustrates a schematic of a pulse oximeter system that incorporates electrical contacts to the skin of a patient, in accordance with one embodiment of the present invention.

As illustrated in the schematic of FIG. 3A, a first aspect of the present invention involves an optical probe 202 which incorporates a number of electrical contacts 341 and 342 that make contact to the skin of the patient when the probe 202 is properly secured. In order to detect a probe-off condition, a probe-off detector module 138 of the pulse oximeter 140 periodically applies a voltage across the contacts 341 and 342 or drives a current. A non-zero current indicates that the patient's skin 344 has closed the circuit between the contacts 341 and 342 and the probe 202 is properly secured. If the probe becomes dislodged, the patient's skin 344 is no longer be in contact with the contacts 341 and 342, resulting in an open circuit.

Figure 3B:
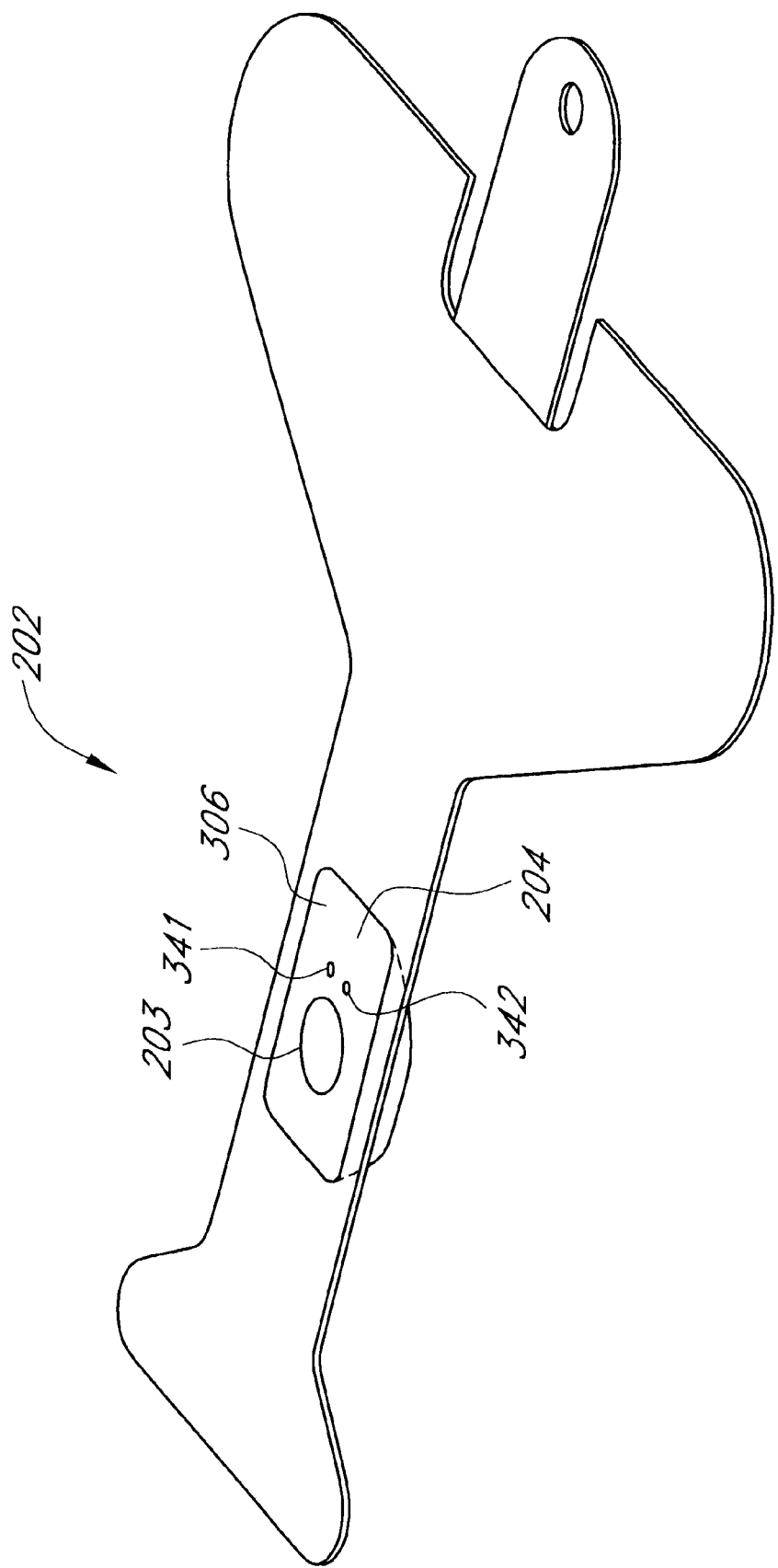
FIG. 3B illustrates a perspective view of an optical probe incorporating electrical contacts to the skin of a patient.

FIG. 3B illustrates one preferred embodiment of an optical probe 202 incorporating one embodiment of the present invention. The present embodiment incorporates a first electrical contact 341 and a second electrical contact 342 in the surface 306 of the central portion 204 of the probe 202. The electrical contacts 341 and 342 are positioned in a location such that contact to a finger or flesh portion of the patient is ensured when the probe 202 is properly attached. In the illustrated embodiment, the contacts 341 and 342 are located proximate the detector aperture 203. In another embodiment, contacts 341 and 342 are on opposite sides of the detector aperture 203. The optical probe 202 also has an emitter aperture 220 through which light of at least two wavelengths passes from LEDs.

Figure 3C:
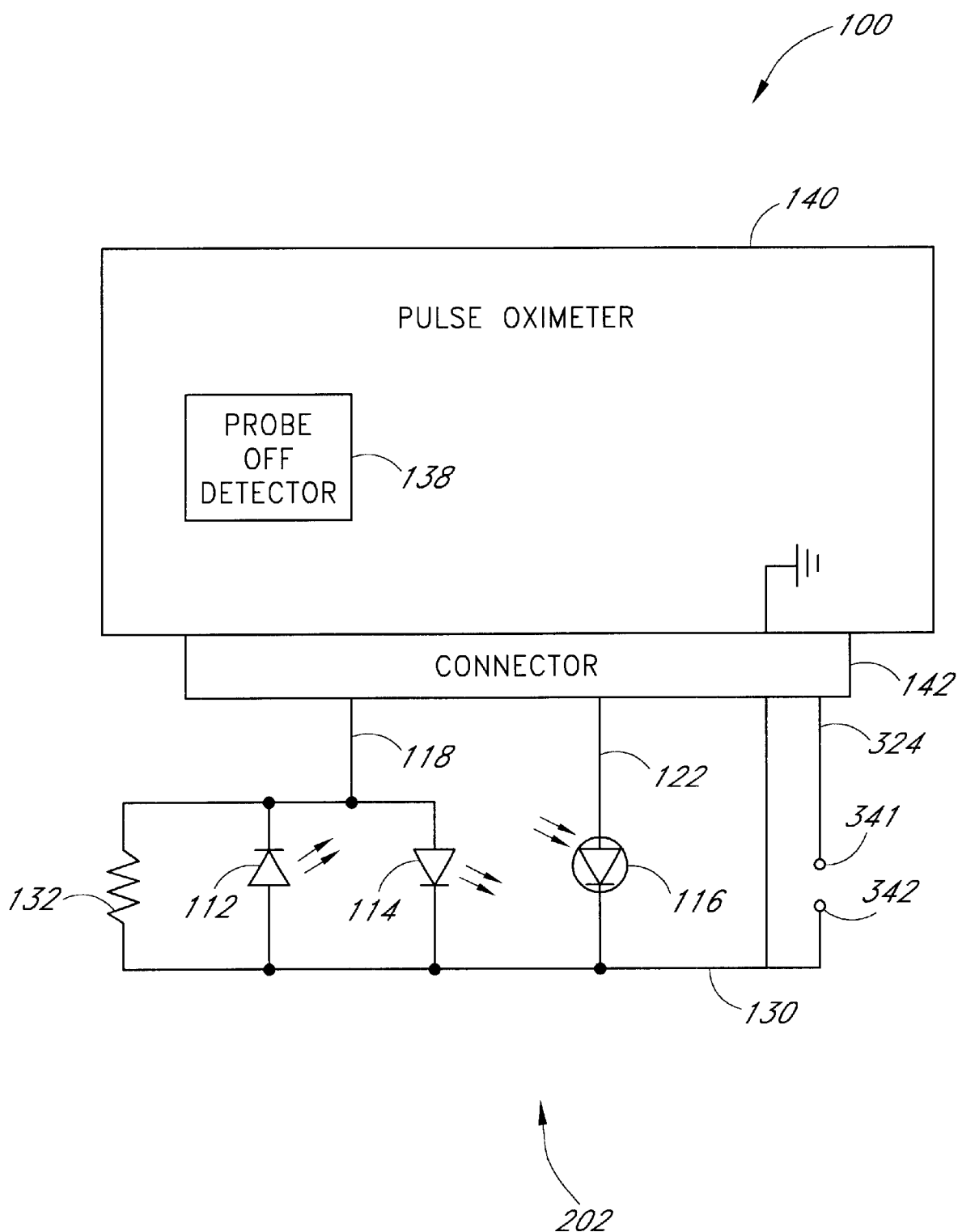
FIG. 3C illustrates a schematic of one embodiment of a pulse oximeter system that incorporates electrical contacts to the skin of a patient.

As illustrated in the schematic diagram of FIG. 3C, the pulse oximeter system 100 of FIG. 1 can be modified to incorporate the first aspect of the present invention by extending an additional lead 324 through the connector 142 to the probe 202. The additional lead can be connected to one contact 341 while the second contact 342 can be wired to the common ground lead 130.

Figure 3D:
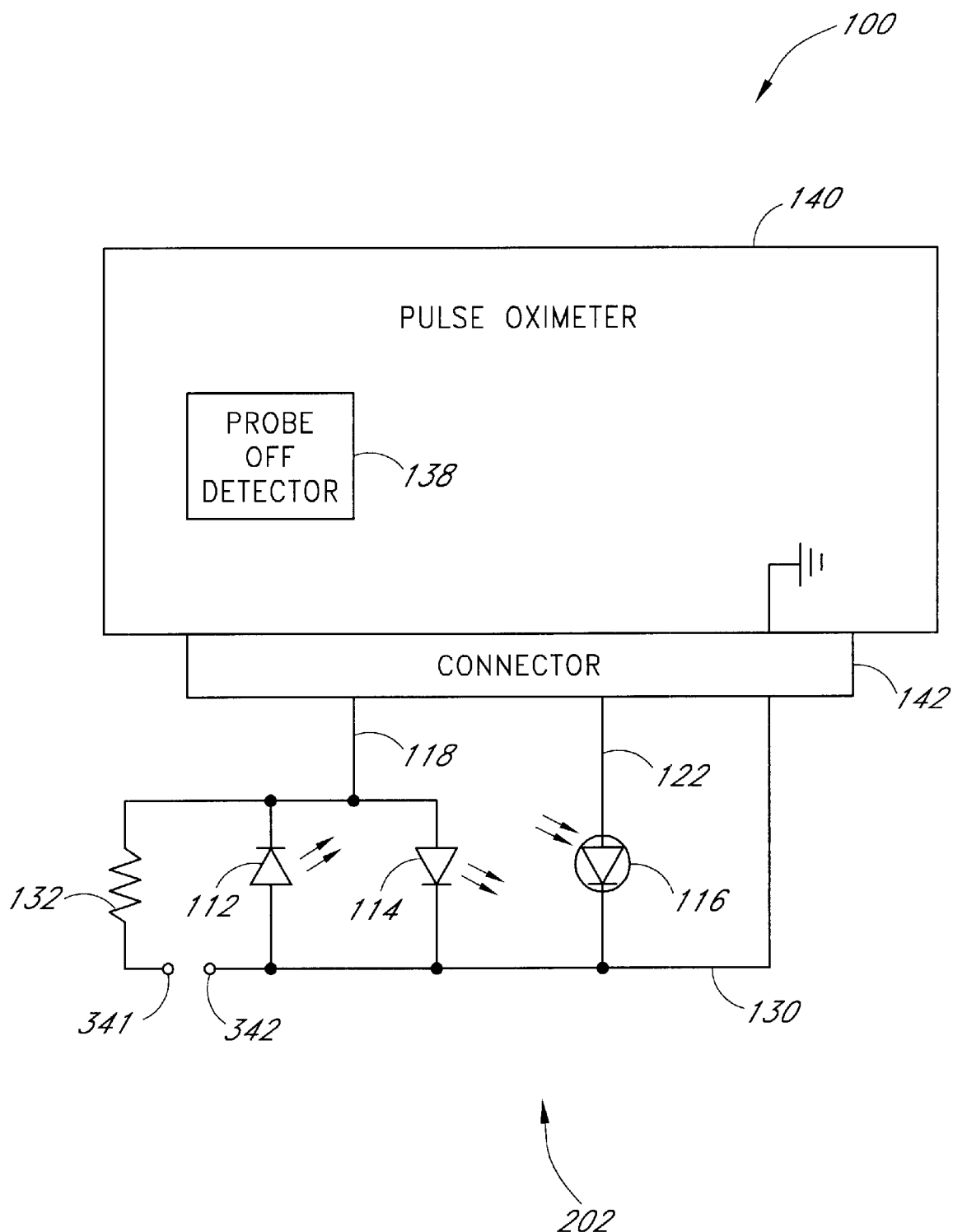
FIG. 3D illustrates a schematic of a preferred embodiment of a pulse oximeter system that incorporates a number of electrical contacts to the skin of a patient.

A schematic diagram of another embodiment of the present invention is illustrated in FIG. 3D. The contacts 341 and 342 can be installed in line within the path of the coding resistor 132. When the patient's skin 344 is in contact with the contacts 341 and 342, the circuit through the coding resistor 132 will be closed; when the patient's skin 344 is not in contact with the contacts 341 and 342, the circuit through the coding resistor 132 will be open. The skin 344 will have some finite resistance between the contacts 341 and 342 that will affect the measured resistance of the coding resistor. As the contacts 341 and 342 are installed in series with the coding resistor 132, any resistance across the contacts 341 and 342 will be added to the resistance of the coding resistor 132 when the pulse oximeter 140 attempts to measure the resistance of the coding resistor 132. The resistance of the skin 344 can effectively be ignored in the measurement of the coding resistor 132, however, by choosing the value of the coding resistor 132 to be substantially larger than the resistance of a patient's skin 344 between the contacts 341 and 342. Alternatively, the acceptable resistance for the coding resistor can be specified as in a range that includes the likely added resistance of the skin in the circuit. In the present configuration, the probe-off detector module 138 of the pulse oximeter 140 can verify that the optical probe 202 is properly secured simultaneously with checking the resistance of the coding resistor 132. An open circuit indicates that the probe has become dislodged, whereas a valid resistance of a coding resistor 132 indicates a proper attachment of the probe 202. If the probe has become dislodged, the pulse oximeter 140 can sound an alarm, display a warning message, or both.

The pulse oximeter 140 is particularly vulnerable to probe-off errors when operating at its highest sensitivity, where even small induced variations in light directly detected from the emitters have sufficient signal strength to be processed as a physiological signal. In a probe-off condition, a detector AC signal can be induced by slight changes in the direct light path between the emitters and the detector. For example, small amounts of patient motion, such as chest movement from breathing, can induce a probe-off AC signal. As another example, "creep" in the probe configuration, such as a folded probe gradually returning to its original unfolded shape after becoming dislodged can also induce a probe-off AC signal.

Figure 3E:
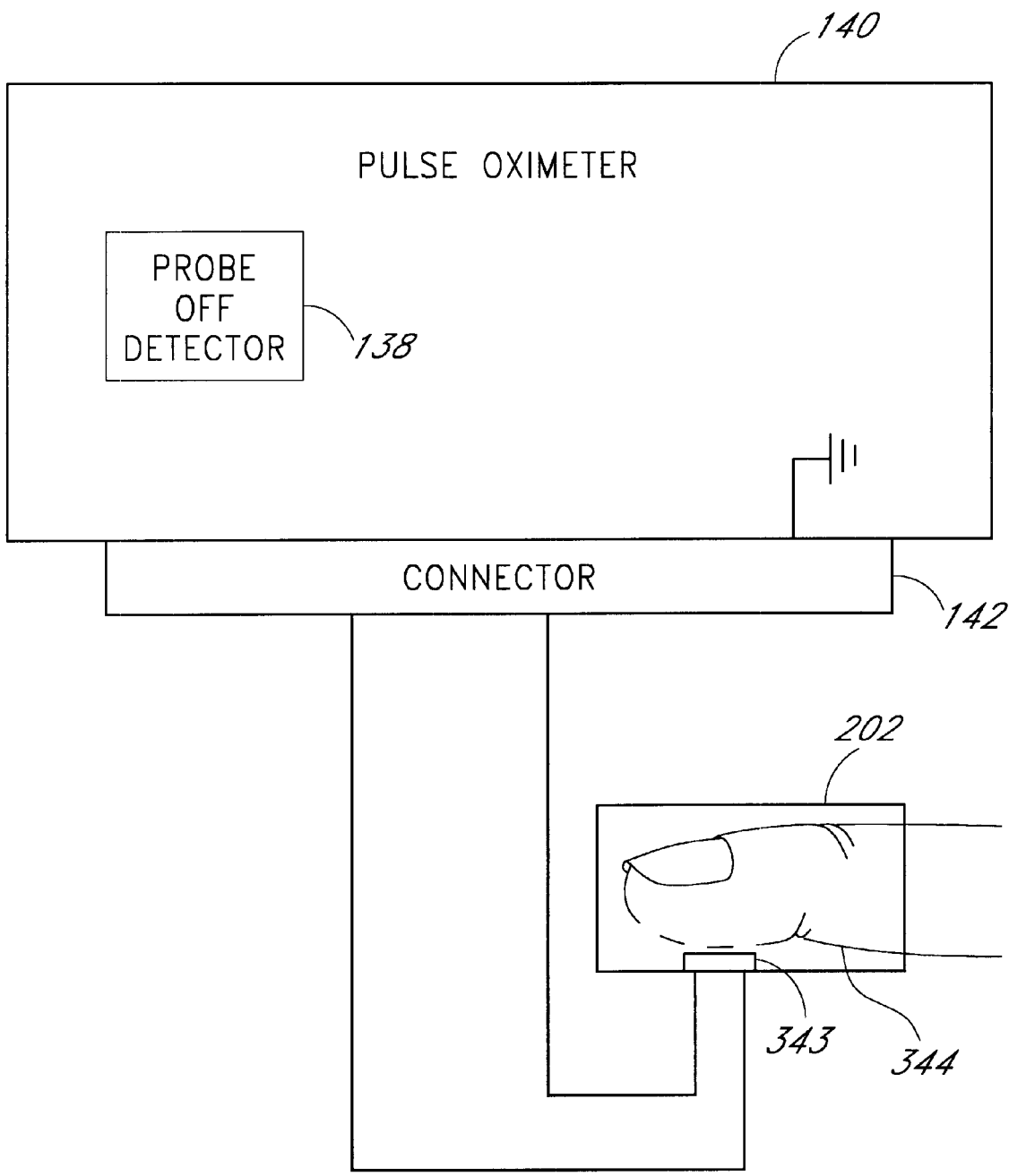
FIG. 3E depicts a generalized schematic of a pulse oximeter that incorporates another embodiment of a contact on a pulse oximeter probe.
Figure 3F:
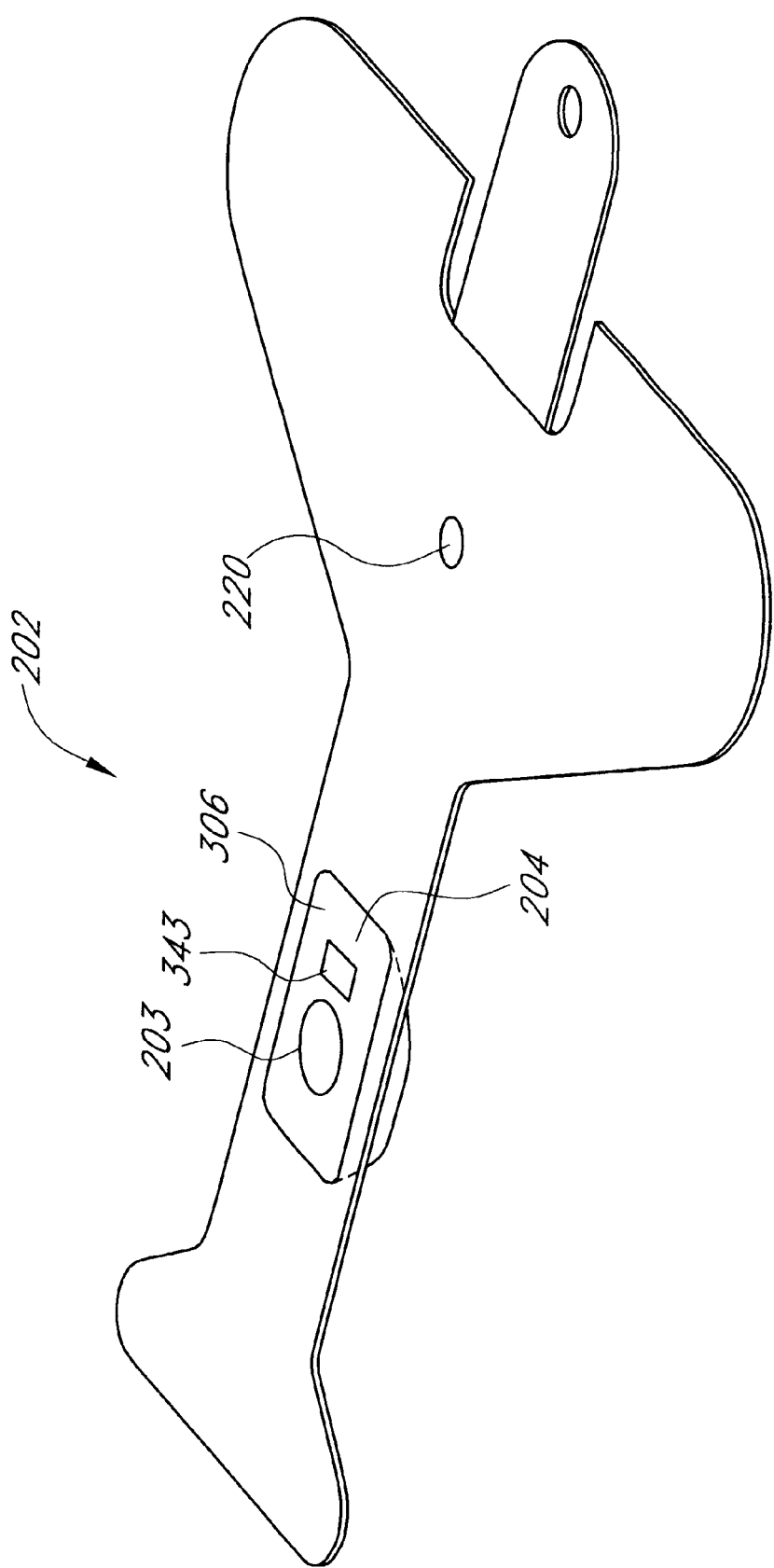
FIG. 3F depicts a perspective view an optical probe incorporating the embodiment of FIG. 3E.

FIGS. 3E and 3F depict a generalized embodiment of the present invention with the same features as described in 3A and 3B, except that the electrical contacts 341, 342 are replaced with a contact sensor 343. The electrical contacts 341 and 342 comprise a specialized case of a contact sensor 343 where skin is involved. The contact sensor 343 may also comprise a piezoelectric sensor, a conductive contact sensor, or any other contact sensors which detect the contact of the tissue material.

Figure 3G:
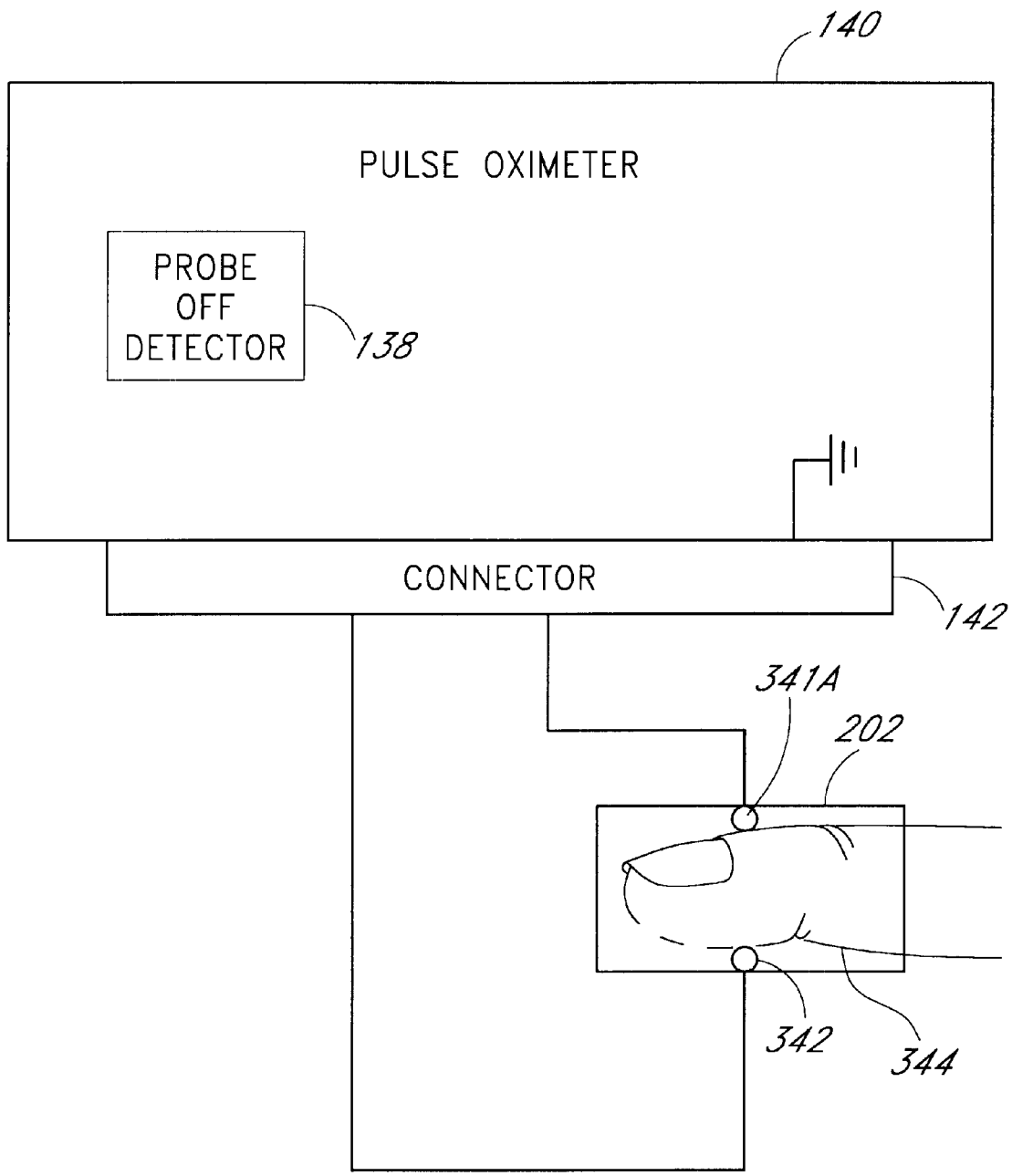
FIG. 3G depicts a generalized schematic of a pulse oximeter system that incorporates another embodiment of a contact sensor in accordance with the present invention.
Figure 3H:
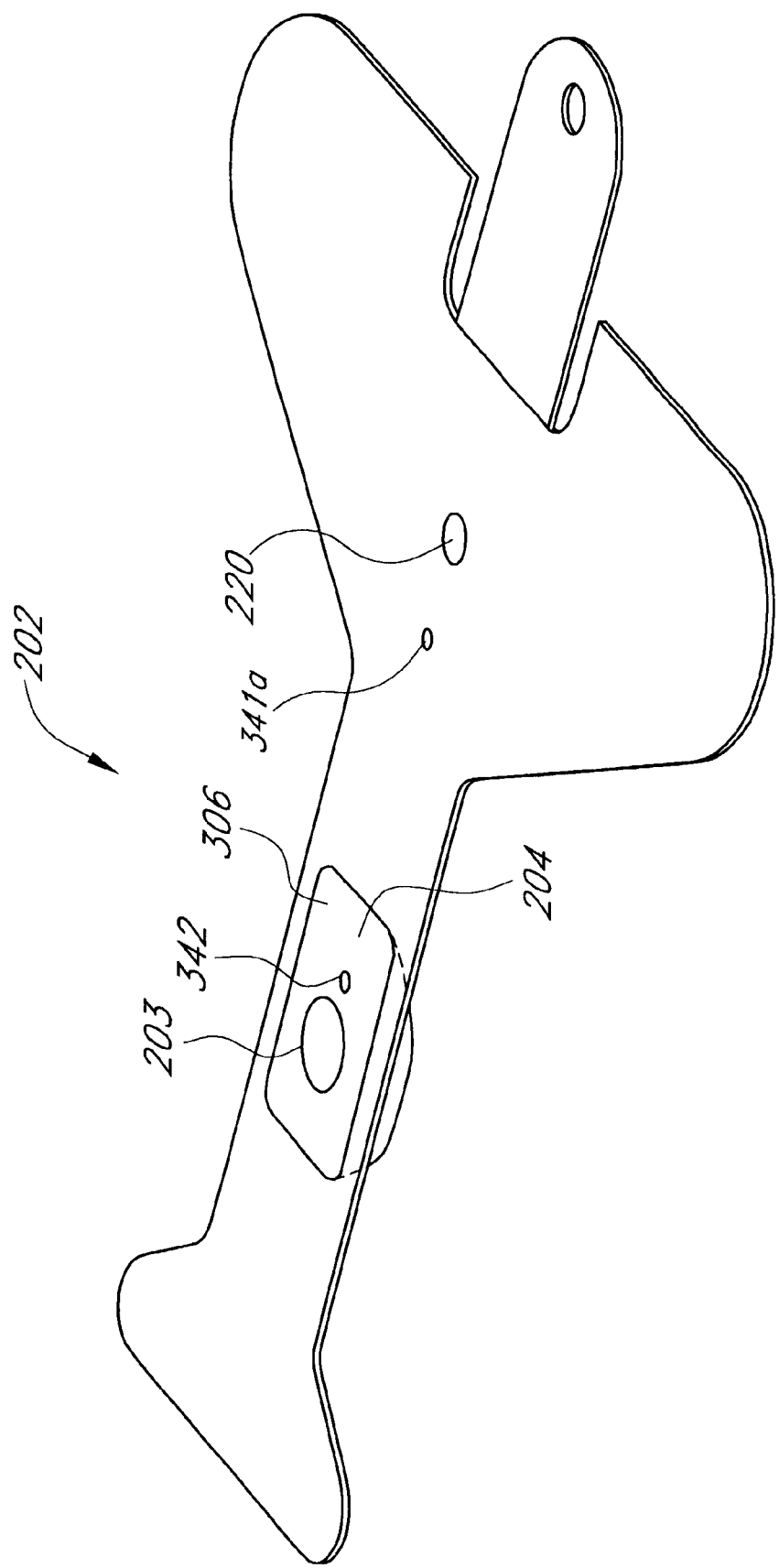
FIG. 3H depicts a perspective view of an optical probe incorporating the contact sensor of FIG. 3G.

FIGS. 3G and 3H depict yet another embodiment of the electrical contact based contact sensor of FIGS. 3A and 3B. FIG. 3G depicts a schematic form with a pulse oximeter 140 and a probe off detector module. FIG. 3H depicts a perspective view of the optical pulse oximeter probe having optical emitters and at least one detector. However, in this embodiment, electrical contact 341A and electrical contact 342 are positioned opposite each other. The electrical contact 341A is positioned near the emitter aperture 220, so as to contact the portion of the tissue material near the emitter 220. The electrical contact 342 is positioned near the detector aperture 203. Similarly, other contact sensors could be positioned, one near the emitter aperture 220 and one near the detector aperture 203.

In one embodiment the electrical contacts 341, 342, 341A are metallic. In another embodiment, these contacts comprise conductive adhesive, or gel based contacts.

Figure 4:
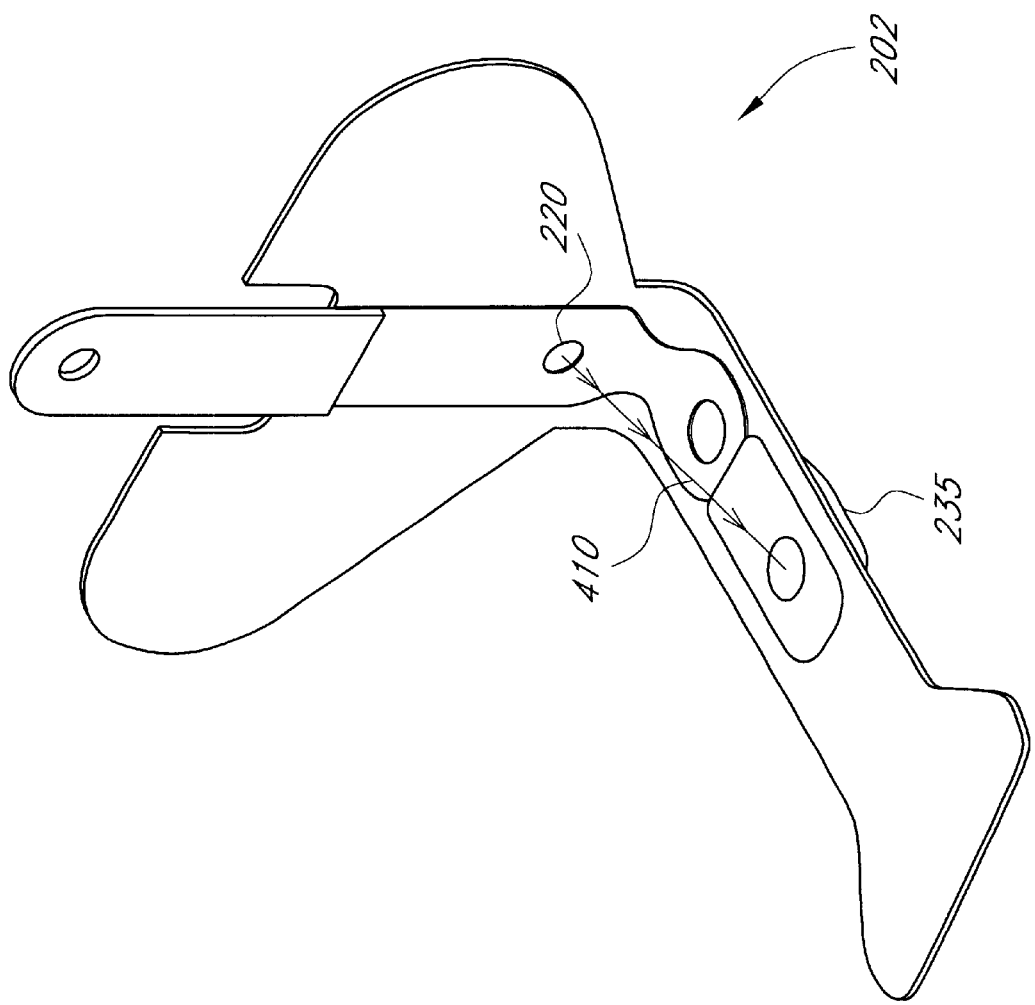
FIG. 4 illustrates a probe that has become unfastened.

FIG. 4 illustrates a probe 202 that has become unfastened. The illustrated probe 202 is shown in a partially unfolded shape that provides an oblique path 410 from the emitter aperture 220 to the detector assembly 235. As a patient moves, or as the probe 202 unfolds, rays of light travelling along the oblique light path 410 may generate an AC signal that could be interpreted by the pulse oximeter 140 as a physiological signal.

Figure 5A:
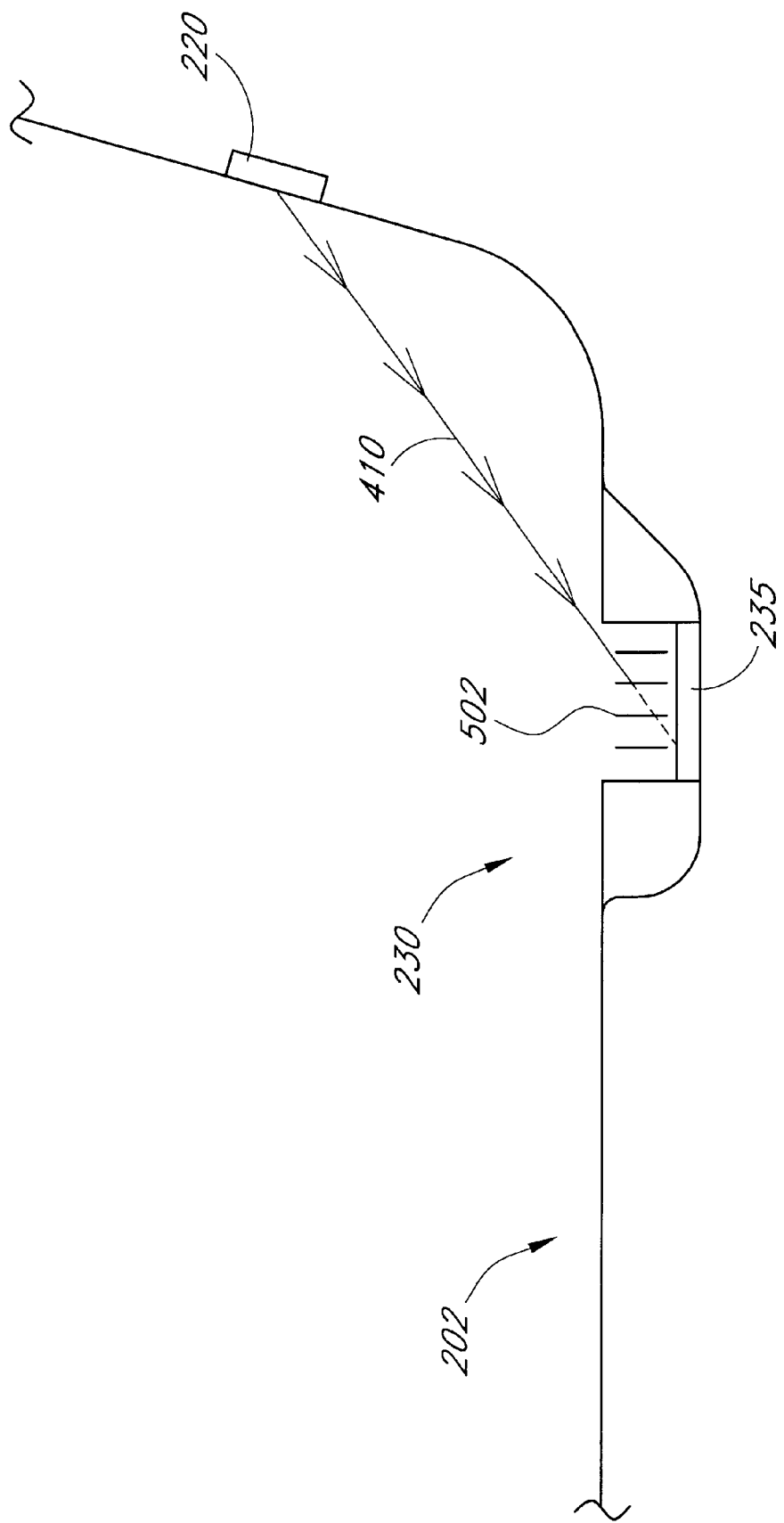
FIG. 5A illustrates a probe wherein a number of louvers are placed in front of the detector assembly.

As illustrated in the cross section of FIG. 5A, a number of louvers 502 are placed in front of the detector assembly 235 within the detector aperture 203 in accordance with a second aspect of the present invention. The louvers 502 block light rays travelling along an oblique path 410 (i.e., light that does not originate from in front of the detector assembly 235). As illustrated in FIG. 5B, if the probe 202 is properly attached, the emitter aperture 220 will be directly in front of the detector assembly 235 and light rays will pass directly through the louvers 502 along a direct path 510.

Figure 5C:
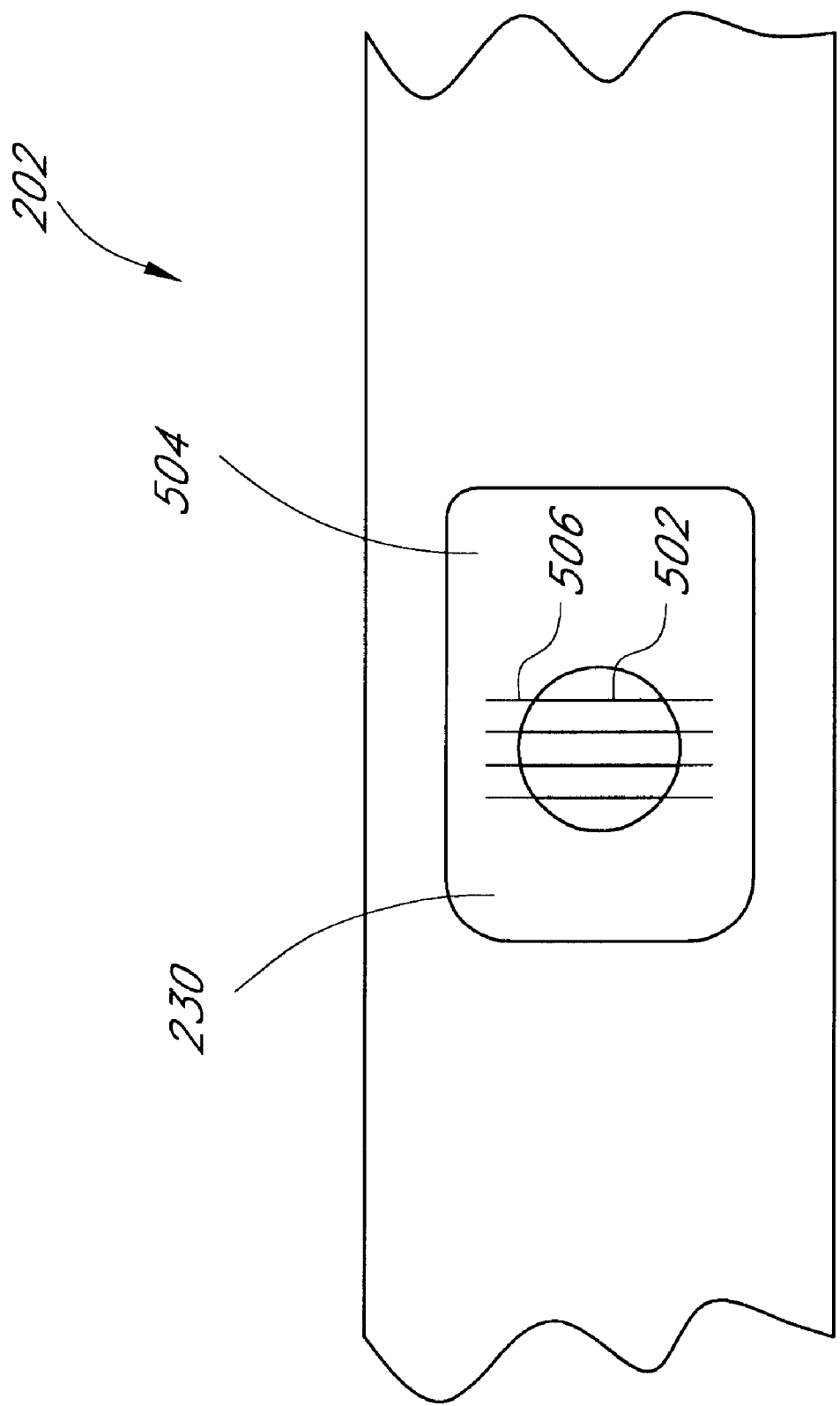
FIG. 5C illustrates a top plan view of a preferred embodiment of a probe wherein a number of louvers are placed in front of the detector assembly

FIG. 5C illustrates a top plan view of a preferred embodiment of this aspect of the present invention. The detector aperture 203 is formed in a plastic body 504 having slots 506 to hold the louvers 502 in place across the detector aperture 203. In a preferred embodiment of the present aspect, the louvers 502 can be created from commercially available "3M Light Control Film."

The louvers 502 of the present aspect advantageously provide a separate or improved method for the pulse oximeter 140 to determine when a probe has become dislodged through monitoring the signal produced by the photodetector 116. If the probe 202 becomes improperly secured, the emitter aperture will likely move from its proper location directly above the detector assembly 235, which will cause any oblique light rays to be blocked by the louvers 502. With no light rays reaching the detector assembly 235, the detector will produce no signal. The probe-off detector 138 of the pulse oximeter 140 can detect the lack of signal and sound an alarm. The louvers 502 also advantageously block oblique light rays that might create a false signal that could be interpreted by the pulse oximeter 140 to be a physiological signal. Accordingly, the louvers 502 reduce or eliminate the possibility of a probe-off condition. The louvers 502 may be used alone or in combination with the contacts described herein.

Figure 6:
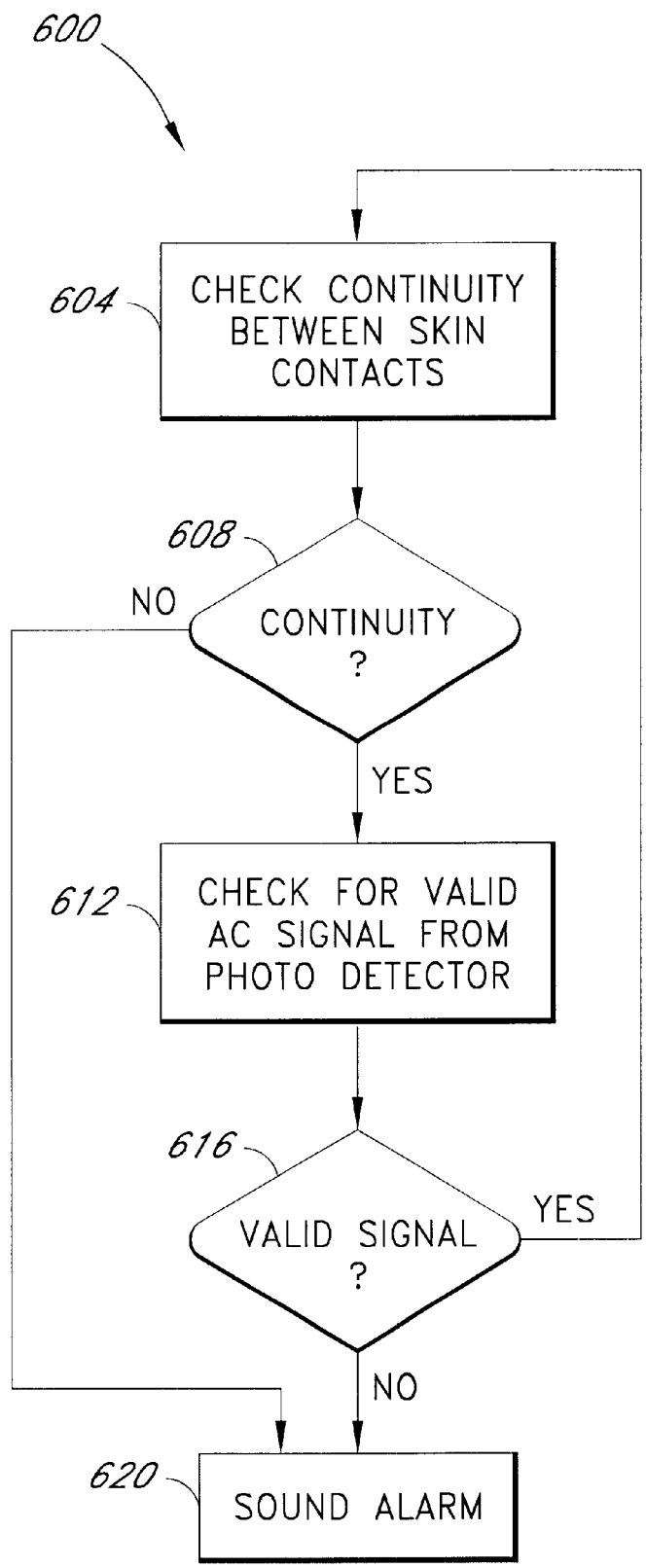
FIG. 6 illustrates a flow chart of the method of detecting a dislodged probe.

FIG. 6 illustrates one embodiment of a method 600 by which a pulse oximeter 140 detects a dislodged probe and/or a probe-off condition. At a step 604, the probe off detector module 138 checks for continuity between the skin contacts 341 and 342. If, at a step 608, there is continuity between the contacts 341 and 342, the oximeter 140 passes control to a step 612. If, on the other hand, there is no continuity at the step 608, the oximeter 140 passes control to a step 620. At step 620 the oximeter 140 sounds an alarm to alert a condition necessitating attention. At the step 612, the oximeter 140 checks for a valid AC signal from the photodetector. If, at a step 616, there is a valid signal, the oximeter 140 passes control back to the step 604 to start the cycle over again. If, on the other hand, there is no valid AC signal at the step 616 the oximeter sounds an alarm at the step 620.

Accordingly, the pulse oximeter checks for and detects dislodgment of a probe and/or a probe-off condition.

While certain exemplary preferred embodiments have been described and shown in the accompanying drawings, it is to be understood that such embodiments are merely illustrative of and not restrictive on the broad invention. Further, it is to be understood that this invention shall not be limited to the specific construction and arrangements shown and described since various modifications or changes may occur without departing from the spirit and scope of the invention as claimed. It is intended that the scope of the invention be limited not by this detailed description but by the claims appended hereto.

What is claimed is:

1. A method for verifying attachment of an optical probe to a patient, the method comprising:
    providing an optical probe, the optical probe having at least two contacts configured to contact a patient's skin when the optical probe is properly attached;
    applying a voltage across the at least two contacts; and
    determining, based upon a measured resistance of a coding resistor, whether the at least two contacts are in contact with the patient's skin.

2. The method of claim 1, wherein the at least two contacts comprise metallic contacts.

3. The method of claim 1, wherein the at least two contacts comprise conductive adhesive contacts.

4. The method of claim 1, wherein the at least two contacts comprise gel-based contacts.

5. The method of claim 1, wherein the at least two contacts are positioned on the patient's skin proximate to a detector aperture in the optical probe.

6. The method of claim 1, wherein the at least two contacts are positioned on the patient's skin proximate to an emitter aperture in the optical probe.

7. The method of claim 1, wherein one of the at least two contacts is positioned on the patient's skin proximate to a detector aperture in the optical probe and the other of the at least two contacts is positioned on the patient's skin proximate to an emitter aperture in the optical probe.

8. The method of claim 1, further comprising generating a visual alarm when the at least two contacts are not in contact with the patient's skin.

9. The method of claim 1, further comprising generating a audible alarm when the at least two contacts are not in contact with the patient's skin.

10. The method of claim 1, further comprising generating at least one of a visual or audible indicator when the at least two contacts are in contact with the patient's skin.

11. A method of detecting that a pulse oximetry probe may not be properly attached to a tissue site, the method comprising:
    providing a pulse oximetry probe having a light emitter, a light detector configured to detect light from the light emitter when the pulse oximetry probe is properly attached, and at least two contacts configured to make contact to a patient's skin when the pulse oximetry probe is properly attached;
    emitting light from the light emitter;
    checking for continuity across the at least two contacts by measuring a resistance of a coding resistor;
    checking for a valid signal from the light detector; and
    determining whether the pulse oximetry probe is properly attached based upon the continuity check and the valid signal check.

12. The method of claim 11, wherein the light detector further includes at least one louver.

13. The method of claim 11, wherein the measuring the resistance of the coding resistor includes measuring the resistance of the patient's skin.

14. The method of claim 11, wherein the measuring the resistance of the coding resistor does not include measuring the resistance of the patient's skin.

15. The method of claim 11, wherein the at least two contacts comprise metallic contacts.

16. The method of claim 11, wherein the at least two contacts comprise conductive adhesive contacts.

17. The method of claim 11, wherein the at least two contacts comprise gel-based contacts.

18. The method of claim 11 wherein the at least two contacts are positioned on the patient's skin proximate to the light detector.

19. The method of claim 11, wherein the at least two contacts are positioned on the patient's skin proximate to the light emitter.

20. The method of claim 11, wherein one of the at least two contacts is positioned on the patient's skin proximate to the light detector and the other of the at least two contacts is positioned on the patient's skin proximate to the light emitter.

21. The method of claim 11, further comprising generating a visual alarm when the pulse oximetry probe is not properly attached.

22. The method of claim 11, further comprising generating a audible alarm when the pulse oximetry probe is not properly attached.

23. The method of claim 11, further comprising generating at least one of a visual or audible indicator when the pulse oximetry probe is properly attached.

24. A pulse oximetry system comprising:
    a pulse oximeter base unit;
    an optical probe configured to be affixed to a body member of a patient;
    at least two electrical contacts located on the optical probe, the electrical contacts configured to make contact to the body member of the patient when the optical probe is properly affixed to the patient; and
    a probe-off detector module configured to check for acceptable continuity across the electrical contacts by measuring a resistance of a coding resistor, thereby determining whether the optical probe is properly affixed to the patient.

25. The pulse oximetry system of claim 24, wherein the coding resistor is in parallel with an emitter of the optical probe.

26. The pulse oximetry system of claim 24, wherein the coding resistor is not in parallel with an emitter of the optical probe.

27. The pulse oximetry system of claim 24, further comprising an indicator for indicating when the optical probe is not properly affixed to the patient.

28. The pulse oximetry system of claim 27, wherein the indicator comprises at least one of an audible or visual alarm.

29. The pulse oximetry system of claim 24, further comprising an indicator for indicating when the optical probe is properly affixed to the patient.

30. The pulse oximetry system of claim 24, wherein the at least two electrical contacts are positioned on the body member proximate to a detector of the optical probe.

31. The pulse oximetry system of claim 24, wherein the at least two electrical contacts are positioned on the body member proximate to an emitter of the optical probe.

32. The pulse oximetry system of claim 24, wherein one of the at least two electrical contacts is positioned on the body member proximate to a detector of t he optical probe and the other of the at least two electrical contacts is positioned on the body member proximate to an emitter of the optical probe.

33. The pulse oximetry system of claim 24, wherein the at least two electrical contacts comprise metallic contacts.

34. The pulse oximetry system of claim 24, wherein the at least two electrical contacts comprise conductive adhesive contacts.

35. The pulse oximetry system of claim 24, wherein the at least two electrical contacts comprise gel-based contacts.

36. A pulse oximeter system for determining proper attachment of a sensor, the pulse oximeter system comprising:
   an oximeter base unit; and
   a probe-off detector module configured to verify proper attachment of a pulse oximetry sensor to a measurement site of a patient by measuring a resistance associated with a coding resistor and a probe-off circuit of the pulse oximetry sensor.

37. The pulse oximetry system of claim 36, wherein the probe-off circuit comprises a contact sensor.

38. The pulse oximetry system of claim 37, wherein the contact sensor comprises a piezoelectric sensor.

39. The pulse oximetry system of claim 36, wherein the coding resistor is in parallel with an emitter of the pulse oximetry sensor.

40. The pulse oximetry system of claim 36, wherein the coding resistor is not in parallel with an emitter of the pulse oximetry sensor.

41. The pulse oximetry system of claim 36, further comprising an indicator for indicating when the pulse oximetry sensor is not properly affixed to the measurement site.

42. The pulse oximetry system of claim 41, wherein the indicator comprises at least one of an audible or visual alarm.

43. The pulse oximetry system of claim 16, further comprising an indicator for indicating when the pulse oximetry sensor is properly affixed to the measurement site.

44. The pulse oximetry system of claim 16, wherein the probe-off circuit comprises two contacts.

45. The pulse oximetry system of claim 44, wherein the two contacts are positioned on the measurement site proximate to a detector of the pulse oximetry sensor.

46. The pulse oximetry system of claim 44, wherein the two contacts are positioned on the measurement site proximate to an emitter of the pulse oximetry sensor.

47. The pulse oximetry system of claim 44, wherein one of the two contacts is positioned on the measurement site proximate to a detector of the pulse oximetry sensor and the other of the two contacts is positioned on the measurement site proximate to an emitter of the pulse oximetry sensor.

* * * * *